(12) United States Patent
Saini

(10) Patent No.: US 7,297,547 B2
(45) Date of Patent: Nov. 20, 2007

(54) ANALYSIS OF METALS IN ACIDIC SOLUTIONS

(75) Inventor: Harmesh K. Saini, Santa Clara, CA (US)

(73) Assignee: Metara, Inc., Sunnyvale, CA (US)

( * ) Notice: Subject to any disclaimer, the term of this patent is extended or adjusted under 35 U.S.C. 154(b) by 0 days.

(21) Appl. No.: 11/178,857

(22) Filed: Jul. 11, 2005

(65) Prior Publication Data
US 2006/0073608 A1    Apr. 6, 2006

Related U.S. Application Data

(60) Provisional application No. 60/615,817, filed on Oct. 5, 2004.

(51) Int. Cl.
*G01N 33/20* (2006.01)

(52) U.S. Cl. ......................... 436/73; 250/281; 250/282; 250/288; 422/69; 422/70; 436/79; 436/80; 436/81; 436/82; 436/83; 436/84; 436/161; 436/171; 436/172; 436/173; 436/174; 436/177; 436/178; 436/183

(58) Field of Classification Search ........ 250/281–282, 250/288; 422/69–70, 82.05, 82.08; 436/73, 436/79–84, 161, 171–174, 177–178, 183
See application file for complete search history.

(56) References Cited

U.S. PATENT DOCUMENTS

| | | | | |
|---|---|---|---|---|
| 2,743,159 A | * | 4/1956 | Lutz | 423/7 |
| 3,156,644 A | * | 11/1964 | Kunin | 210/638 |
| 3,828,800 A | * | 8/1974 | Litzinger | 131/334 |
| 4,515,943 A | * | 5/1985 | Miya et al. | 536/26.24 |
| 6,492,551 B1 | * | 12/2002 | Paatero et al. | 562/609 |

FOREIGN PATENT DOCUMENTS

JP    5-220477    *    8/1993

OTHER PUBLICATIONS

Kunin, R. et al, Journal of the American Chemical Society 1947, 69, 2874-2878.*
Gustafson, R. L. et al, Industrial & Engineering Chemistry Fundamentals 1970, 9, 221-229.*
Kunin, R. et al, Chemical Engineering 1971, 78, 67-69.*
Miller, D. G., Cooling Towers 1975, 2, 6-10.*
Osipova, T. I. et al, Journal of Analytical Chemistry, 1978, 33, 690-693.*
Hubicka, H., Solvent Extraction and Ion Exchange 1988, 6, 361-374.*

(Continued)

*Primary Examiner*—Arlen Soderquist
(74) *Attorney, Agent, or Firm*—Jonathan W. Hallman; MacPherson Kwok Chen & Heid LLP

(57) ABSTRACT

In one embodiment, a method of neutralizing the matrix of an acidic solution including at least one metal using a weak anion exchange resin is provided. The method includes the acts of: activating the weak anion exchange resin with a weakly acidic metal complexing reagent, the weakly acidic metal complexing reagent partially disassociating into protons and metal complexing anions, whereby some functional groups in the weak anion exchange resin are protonated and bind with the metal complexing anions; and neutralizing a sample of the acidic solution with the activated weak anion exchange resin.

19 Claims, 4 Drawing Sheets

OTHER PUBLICATIONS

Hubicka, H. et al, Hungarian Journal of Industrial Chemistry 1992, 20, 113-116.*
Igarashi, H. et al, Nuclear Technology 1993, 102, 287-296.*
Yoshida, H. et al, Industrial & Engineering Chemistry Research 1994, 33, 854-859.*
Gensler, M. et al, Journal of Agricultural and Food Chemistry 1995, 43, 2662-2666.*
Toda, E. et al, Analytica Chimica Acta 1996, 333, 51-58.*
Ruddick, C. L. et al, Synthesis 1996, 1359-1362.*
Barnowski, C. et al, Journal of Analytical Atomic Spectrometry 1997, 12, 1155-1161.*
Svete, P. et al, Analyst 2001, 126, 1346-1354.*
Hubicki, Z. et al, Desalination 2003, 155, 121-130.*
Fritz, J. S. et al, Talanta 1971, 18, 541-548.*
Holl, W. H. et al, Ion Exchange at the Millennium, Proceedings of IEX 2000, 8th, Cambridge, United Kingdom, Jul. 16-21, 2000, 377-385, Editor: Greig, J. A., Publisher: Imperial College Press, London, UK.*

* cited by examiner

ANALYSIS OF METALS IN ACIDIC SOLUTIONS

RELATED APPLICATIONS

This application claims the benefit of U.S. Provisional Application No. 60/615,817, filed Oct. 5, 2004, the contents of which are hereby incorporated by reference.

BACKGROUND

1. Field of Invention

The present invention generally relates to analysis of solutions. More particularly, the present invention relates to the analysis and detection of metals in acidic solutions.

2. Discussion of the Related Art

The matrix of a solution sample has a pronounced effect on the detection or quantification of trace analytes by modem analytical instruments. For example, an acidic matrix may obscure the detection and quantification of the metals. The difficulty of detecting, identifying, and/or measuring metals in acidic matrix exists for a number of different analytical tools. For example, an acidic matrix can obscure the detection and quantification of trace metals in ion chromatography. Acidic matrices are also problematic in mass spectrometry, such as inductively-coupled-plasma mass spectrometry.

Mass spectrometry is generally the technique of choice for measurement of parts-per-billion (ppb) and sub-ppb levels such as parts-per-trillion (ppt) of elements and compounds in solutions. For example, the present assignee, Metara, Inc., has developed an automated in-process mass spectrometry (IPMS) tool that for the first time allows users such as semiconductor manufacturers to detect and quantify the chemistry of wet process baths and cleaning solutions. Unlike traditional mass spectrometry instruments, the IPMS technique is automated and requires no human intervention. In contrast, the use of traditional mass spectrometers such as an inductively-coupled-plasma mass spectrometer (ICP-MS) requires hands on attention from highly-trained personnel.

The use of ICP-MS is typically "open loop" in that a calibration curve is first established by the users. In general, progressively concentrated (or diluted) solutions of the analyte of interest are processed through the ICP-MS instrument and the results recorded. For example, a 10 ppm solution may be processed, then a 20 ppm solution, and so on. Having established this calibration curve, a user may then analyze the solution of interest. By comparing response from the analyte to the calibration curve, a user may determine the amount of the analyte. If, for example, the response lies halfway between the 10 ppm and 20 ppm calibration curve recordings, a quantification of 15 ppm may be assumed.

But ICP-MS tools are prone to response shifts over time. Moreover, there may be response shifts caused by the difference between the matrices of the calibration standard and the sample. For example, if the acidic matrix shifts in composition, the calibration process must be repeated. These response shifts may be rapid, requiring frequent re-calibrations by experienced technicians. Thus, traditional mass spectrometry analysis was inappropriate for applications requiring continuous and unattended operation such as in semiconductor manufacture. In contrast to traditional techniques, however, IPMS instruments are "closed loop" and thus do not suffer from response shifts.

In an IPMS instrument, a processor controls an automatic sampling of the solution of interest, spiking the sample with a calibration standard, ionizing the spiked sample, processing the ionized spiked sample through the mass spectrometer to produce a ratio response, and analyzing the ratio response to determine the amount of an analyte in the sample. Unlike prior art open loop techniques, response drifts are not a problem—the drift affects the spike and sample in the same fashion and is thus cancelled in the ratio response. Thus, automated operation may be implemented without the necessity of manual intervention or recalibration. In addition, stable and reliable operation is assured by, in one embodiment, the use of atmospheric pressure ionization (API) such as electrospray to ionize the spiked sample. Moreover, the use of API enhances the characterization of molecular species. Furthermore, the IPMS technique is applicable to the analysis of analytes in either trace or bulk concentrations.

Despite the novel and advantageous properties of the IPMS technique, challenges remain in the detection and analysis of metals in an acidic matrix using this technique. Moreover, these challenges are also present in other analytical techniques such as ion chromatography. An example of an acidic matrix is a commonly-used cleaning solution during semiconductor manufacture that is known as Standard Clean 2 solution (SC2), which is a solution of hydrochloric acid (HCl), hydrogen peroxide ($H_2O_2$), and water in varying ratio. SC2 may be used to remove the metallic residues from the surface of silicon wafers by forming soluble chloride complexes. The most common ratio for SC2 used in semiconductor manufacturing is one part of 37% HCl to one part of 30% $H_2O_2$ to six parts of ultra pure water (UPW).

The continuous decrease in the geometry of semiconductor devices requires increased control of the contaminants in process solutions such as SC2. Control over the contaminants is important because SC2 comes in direct contact with the electronic circuitry during device fabrication. Thus, the quantitative determination and management of metallic contaminants in fresh and spent SC2 solutions is of immense importance, for example, in the optimization of semiconductor manufacturing yields.

Due to the high matrix of protons and chloride ions in the highly acidic SC2 solution, an online determination of trace levels of many metals is very difficult. Such a matrix obscures the analysis of metals in analytical instruments such as mass spectrometers or ion chromatographs. For example, because the metals will not be ionized in an electrospray ionization process, a corresponding mass spectrometer cannot measure or detect them. Moreover, even if other types of ionization such as inductively-coupled plasma ionization are used, the corresponding mass spectrometer cannot be subjected to such a harshly acidic matrix without instrument damage and/or interference problems. Thus, the analysis of metals in such matrices often involves the dilution of the matrix to reduce the matrix effect. But dilution of ultra trace concentrations of metals tends to dilute the metal concentrations to immeasurable levels. The background noise overwhelms the diluted ultra trace concentrations such that the mass spectrometer cannot detect or accurately characterize them. As an alternative, the matrix may be eliminated by heat and/or evaporation in an offline process. But volatile species such as boron or mercury are then lost. Moreover, it usually requires 24 to 48 hours to complete the sample preparation for the analysis in such instances. Accordingly, in most cases, if a problem is detected, such as impurities in the SC2, processing of defective product will have occurred for some time such that potential losses will be high.

Regardless of the analytical tool used for the analysis of acidic matrices, another problem with offline analysis is maintaining the integrity of the SC2 sample starting from collection to the end of analysis. For example, SC2 cleaning is typically done at elevated temperatures, between about 60° C. to about 75° C., and at this temperature the matrix of SC2 is dynamic in nature such that the components of the SC2 are continually reacting with other components and can change over time and with temperature. Thus, by the time the sample reaches a laboratory for analysis, the sample may not be in a representative formulation as it was at the time of collection. In addition, the SC2 matrix is a strong absorption media for airborne soluble contaminants such that if samples are exposed to air at any stage during sampling, transportation, or analysis, the matrix of the sample may be altered or contaminated. Moreover, the cleanliness of the sampling containers is important and a large amount of time and money is spent on cleaning sampling containers. Also, metals present in the sample solution may plate out or adsorb on the walls of the container. Thus, the amount of time the sample is allowed to sit in the sampling container before being analyzed can also affect the analysis outcome. It has been reported that even the cleanest of sampling containers can leach out many undesirable contaminants. Finally, offline elimination, neutralization, or modification of matrixes generally poses a high risk of contamination or sample modification that can affect the integrity of the sample and the accuracy of the subsequent analysis for all of the reasons stated above. Thus, offline analyses of metals in acidic matrices are problematic.

Accordingly, there is a need in the art for improved techniques for detecting and characterizing metals in acidic matrices.

SUMMARY

A weak anion exchange resin process is disclosed that neutralizes an acidic solution. The metal(s) may comprise metal cations or metal complexes. In this process, the resin is activated using a weakly acidic metal complexing reagent. Some of the functional groups in the resin are thereby protonated and bind to a resulting metal complexing reagent anion. Advantageously, the activated resin then neutralizes the acidic solution such that the metal(s) may be detected or characterized while the activation of the resin limits trapping, adsorption, and precipitation of metal(s) within the activated weak anion exchange resin. The activated resin may then be regenerated using a strongly basic solution such as ammonium hydroxide such that samples of the acidic solution may be continually analyzed using the weak anion exchange resin.

These and other features and advantages of the present invention will be more readily apparent from the detailed description of the embodiments set forth below taken in conjunction with the accompanying drawings.

BRIEF DESCRIPTION OF DRAWINGS

Use of the same or similar reference symbols in different figures indicates identical or similar items. It is further noted that the drawings may not be drawn to scale.

DETAILED DESCRIPTION

Figure 1:
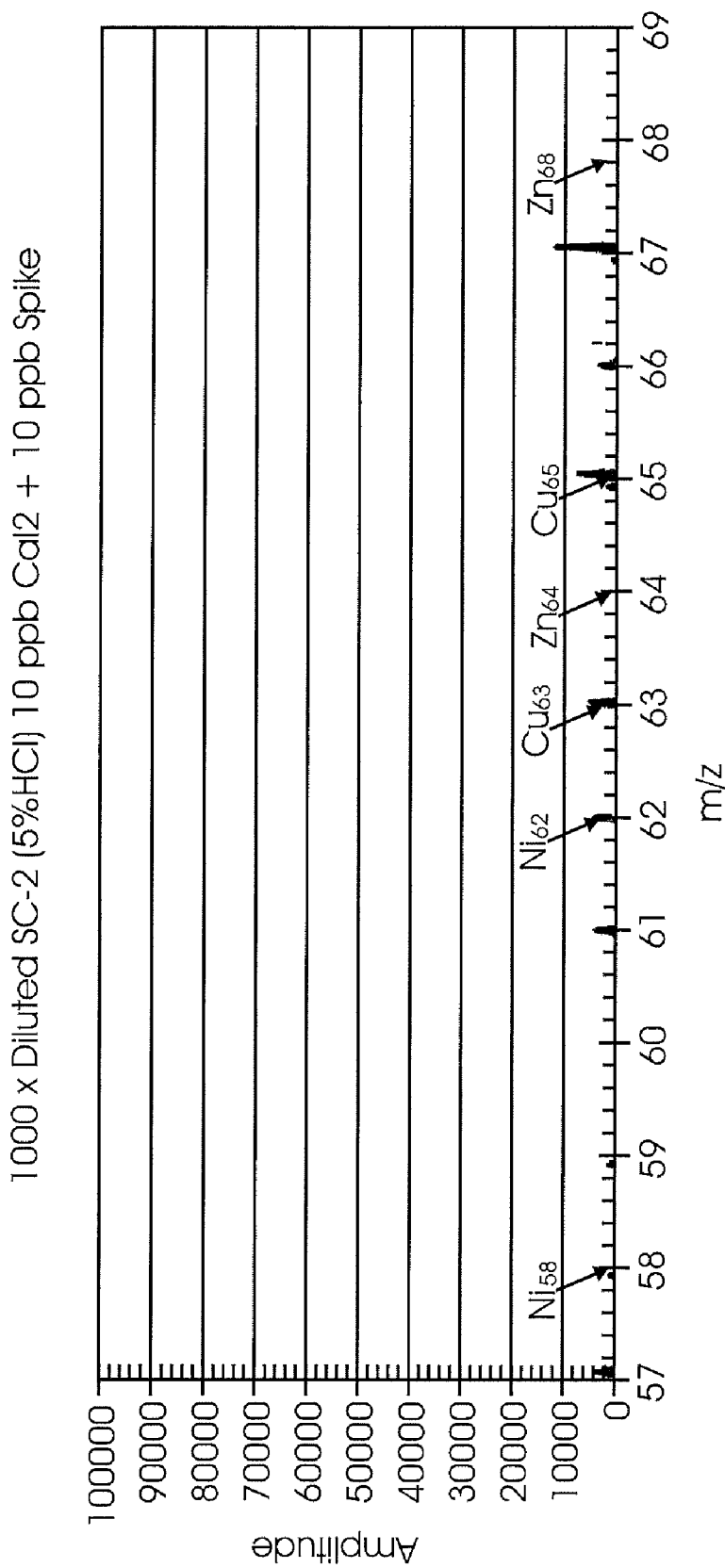
FIG. 1 shows the mass spectrum for an SC-2 solution, wherein the acidic matrix of the SC-2 solution has been reduced according to a conventional dilution technique.

Reference will now be made in detail to one or more embodiments of the invention. While the invention will be described with respect to these embodiments, it should be understood that the invention is not limited to any particular embodiment. On the contrary, the invention includes alternatives, modifications, and equivalents as may come within the spirit and scope of the appended claims. Furthermore, in the following description, numerous specific details are set forth to provide a thorough understanding of the invention. The invention may be practiced without some or all of these specific details. In other instances, well-known structures and principles of operation have not been described in detail to avoid obscuring the invention.

It should also be understood that the application of this invention allowing improved analytical capability of metals in acidic solutions is not limited to any one analytical method. The use of any analytical method that is affected by acidic matrices, either by suppression of analyte signals, by matrix modification of analyte signals, by damage to the instrument or by any other artifact will benefit from this invention.

Processing acidic matrices with an ion exchange resin avoids the problems associated with prior art analyses of metals in such matrices. In general, a number of problems are presented by the use of ion exchange resins in the analysis or detection metals in such matrices. For example, the active groups in the resin may adsorb the metals. In addition, the metals may be trapped in the resin voids or precipitated through reaction with, for example, hydroxide ions. In addition, the metals may be oxidized to form precipitates. These trapping, adsorption, and precipitation effects are quite problematic in the analysis of metals in acidic matrices.

To avoid these problems with ion exchange resins, a weak anion exchange resin is used to neutralize the acidic matrix. In general, an ion exchange resin is an organic polymer to which active groups have been covalently attached. Depending on the properties of these groups, an ion exchange resin may be classified as either a cation or anion exchange resin. In an anion exchange resin, the functional or active groups that have been covalently bonded to the resin backbone are positively charged so that they may exchange negatively charged counter ions (anions). An anion exchange resin may be classified as either a weak or strong anion exchange resin depending upon the basicity of the active groups. As suggested by the name, the active groups in a weak anion exchange resin are weakly (rather than strongly) basic. Generally, a weak anion exchange resin uses tertiary amines or polyamines as the functional groups but it will be appreciated that numerous other functional or active groups having a sufficiently weak basicity (and suitability for covalent bonding to the resin) may also be used.

To form an ion exchange column, the weak anion exchange resin is packed in a suitable column such as one constructed from PEEK of PFE tubing. Alternatively, a column need not be used should a batch mode of operation be desired. In a batch mode, the resin need merely be contained within a suitable container. To avoid the problems associated with trapping, adsorption, and/or precipitation of metals by an ion exchange resin, the weak anion exchange resin is first activated with a solution of a weakly acidic metal complexing reagent. As used herein, a "weakly" acidic metal complexing reagent refers to a reagent having a pKa whose relationship to the pKa for the functional groups in the exchange resin is such that a substantial portion of the functional groups are left un-protonated after exposure to the weakly acidic metal complexing reagent.

Regardless of the particular weakly acidic metal complexing reagent used to activate the resin, the resulting activated resin will have a portion of its functional groups protonated. This protonation requires dissociation of the weakly acidic metal complexing reagent, resulting in the formation of a metal complexing anion and a protonated functional group. This anion will have a certain binding affinity to the protonated functional group (such as a protonated tertiary amine) as known in the arts.

The activated resin may then be used to reduce the matrix in acidic solutions. To neutralize the acid in the matrix, the activated resin should have sufficient number of un-protonated functional groups. For example, as discussed previously, an SC2 solution includes hydrochloric acid (HCL) as a constituent. Because hydrochloric acid is a relatively strong acid, it will protonate virtually all the non-protonated functional groups in the resin that remain after treatment by the weakly acidic cation complexing agent. These protonated functional groups then bind to the chloride anion formed from the donation of the proton from the HCl compound. The resulting treated SC2 solution that elutes from the column is thus virtually neutral in pH, the HCl molecules being bound to the functional groups in the resin. It should be noted that there need not be a complete removal of the acidic matrix to enable detection or characterization of metals—the degree of matrix removal necessary will depend upon the particular analytical instrument that will be used to process the neutralized matrix. As used herein, "neutralized" shall thus not refer to a pH of 7.0 but instead to a pH at which the proton concentration is tolerable for the associated analysis. For example, a given analytical tool may be able to detect metals quite accurately if the acidic matrix is neutralized to a pH of just 6.5.

With respect to the analysis or detection of metals in acidic matrices, suitable organic and inorganic weakly acidic metal complexing reagents to activate the resin include formic acid, acetic acid, oxalic acid, glycolic acid, ethylenediaminetetraacetic acid (EDTA), nitrotriacetic acid (NTA), diethylenetriaminepentaacetic acid (DTPA), ethylenediamine (EDA), glycine, and iminodiacetic acid (IDA). For example, acetic acid may be used to activate a column packed with the weak anion exchange resin. Because of the weak acidity of the metal complexing reagent, it is believed that only a relatively small percentage of the functional groups in the resin will be protonated. These positively-charged functional groups (such as positively-charged tertiary amines) may then adsorb or bind with the metal complexing anion formed after donation of the proton by the weakly acidic metal complexing reagent.

Note that one could reduce undesirable proton levels in harshly acidic matrices by simply eluting the acidic solutions through a column packed with a weak anion exchange resin. But recall the problems discussed previously such as metal retention and trapping, precipitation, and oxidation, which cause undesirable memory effects and other errors in the detection and quantification of the trace metal concentrations. If an anion exchange resin were simply used to eliminate an acidic matrix without any other processing, these trace metal analysis problems would remain. However, trace metal analysis is enabled by the initial activation of the resin by the weakly acidic metal complexing reagent. It is believed that this treatment leaves a relatively small percentage of the functional groups in the resin already protonated and associated with the resulting metal complexing anion. It is believed that this metal complexing anion will have a weaker binding affinity to the protonated functional group than will the chloride anion in the SC2 solution. Thus, the chloride anion exchanges with the metal complexing anion. The majority of the metal complexing anions will thus combine with the remaining protons in the SC2 solution to form the non-ionized metal complexing reagent because the bulk of a weak acid in solution does not disassociate into protons and anions. Those metal complexing reagent anions that are disassociated are then free to complex with and stabilize the metals. Advantageously, the complexing of the metal complexing anion such as acetate with metals is a soft bond such that it is easily disassociated even in a relatively gentle ionization process such as electrospray ionization. Moreover, because the metal complexing reagent is weakly acidic, the pH is kept substantially neutral, for example a pH of 6.7.

It is further believed that the weakly acidic metal complexing reagent provides a further benefit besides complexing the metals in the treated solution. For example, a weak anion exchange resin will typically have a certain concentration of hydroxide ions distributed through the resin. For example, although a tertiary amine is only weakly basic, it is basic nonetheless and thus will have a tendency to ionize with a water molecule such that the tertiary amine becomes protonated and a hydroxide anion is produced. However, activation of the weak anion exchange resin with the weakly acidic metal complexing reagent eliminates these hydroxide ions from the resin prior to treating the acidic matrix. In contrast, consider what could happen should the resin not be activated by the weakly acidic metal complexing reagent. As the acidic matrix flows into a column of such un-activated resin, any hydroxide ions near the entry port of the column will be eliminated by the acid matrix. However, the matrix continues to be neutralized as it flows through the column such that the solution near the exit port of the column will have little acidity. Thus, hydroxide ions could still be present near the exit port within the resin. These hydroxide ions would thus be available to react with metals, thereby causing precipitates and hampering the ability to detect and/or characterize trace metals.

Figure 2:
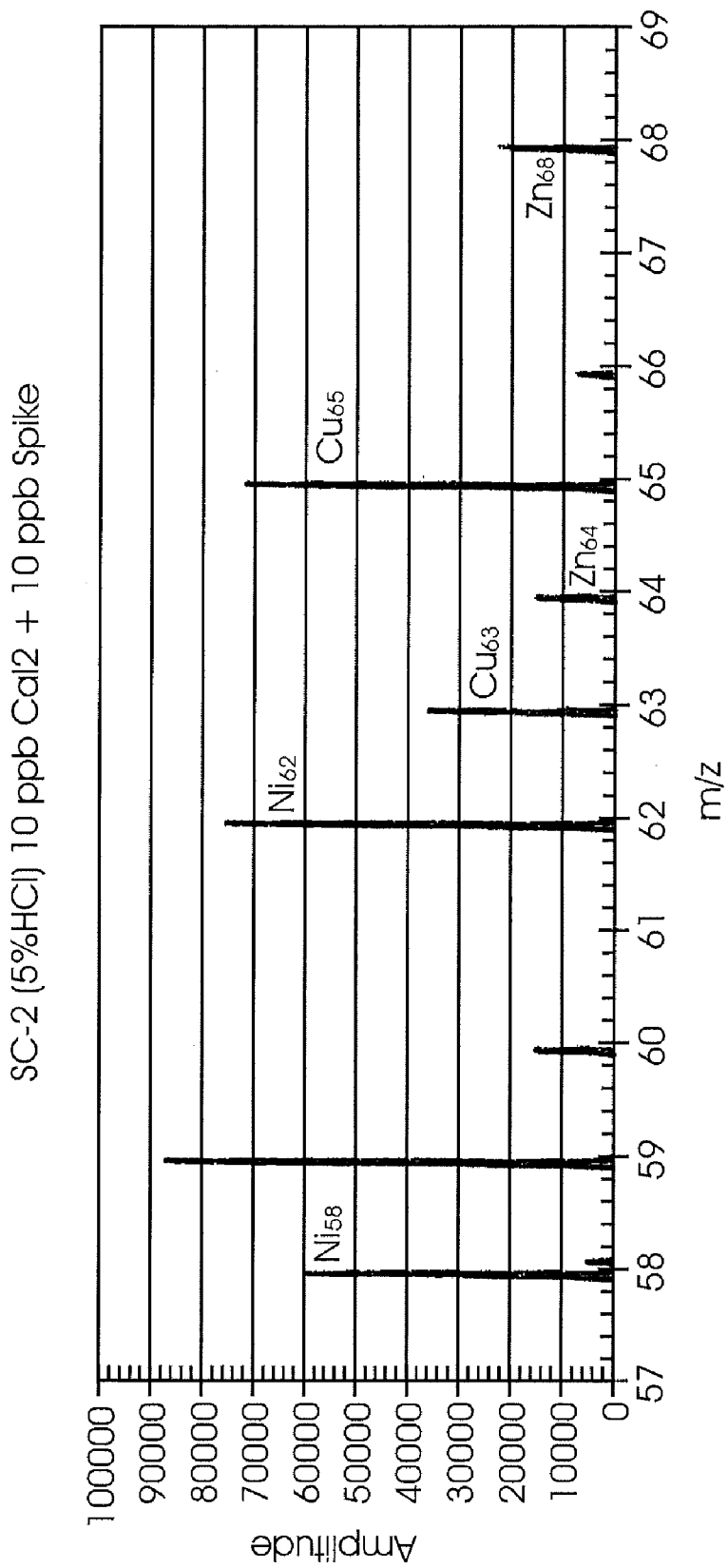
FIG. 2 shows the mass spectrum for an SC-2 solution, wherein the acidic matrix of the SC-2 solution has been reduced in accordance with an embodiment of the invention.

Regardless of the function for the weakly acidic metal complexing reagent (whether it is one of metal complexing or hydroxide ion reduction or a combination of both), the benefits achieved by activating the weak anion exchange resin are dramatic. For example, FIG. 1 illustrates a mass spectrum resulting from a conventional dilution analysis of SC-2 solution. To reduce the matrix effect, the SC-2 has been diluted 1000 times and then spiked with a 10 ppb calibration standard (Ni, Cu, and Zn) and a 10 ppb IDMS spike. The resulting sample was then electrospray ionized and processed through a mass spectrometer. Inspection of FIG. 1 indicates that the spectral response for the metals does not exceed an amplitude of 10,000. In contrast, FIG. 2 illustrates the mass spectrum for an SC-2 solution with the same calibration standard and spike. However, rather than dilute the original SC-2 sample 1000 times to reduce the matrix, the spiked SC-2 sample was processed through a column of activated weak anion exchange resin. The resulting sample was then electrospray ionized and processed through the same mass spectrometer (with the same tunings) as used for FIG. 1. Advantageously, the spectral response for the metals shown in FIG. 2 has increased at least 10-fold over the prior art dilution technique of FIG. 1.

Having treated the SC2 solution, the weak anion exchange resin is easily regenerated with an appropriate strong base such as ammonium hydroxide, sodium hydroxide, or methylamine. In the regeneration of an anion exchange resin, the protonated basic sites are returned to their neutral basic states. For example, a protonated tertiary amine would be reduced to a neutral state upon regeneration. The regenerated column may then be re-activated by treatment with the weakly acidic metal complexing reagent to be ready to neutralize another sample of acidic matrix while stabilizing the trace metals.

As known in the art, the polymer backbone of a weak anion exchange resin may be based on synthetic polymers such as styrene-divinylbenzene copolymer, acrylic, polysaccharides, or many other suitable polymers. A weak anion exchange resin is generally supplied in the form of beads, which may either be dense (gel resins) or porous (macroporous resins). The technique disclosed herein is relatively insensitive to the particular form of the beads.

Figure 3:
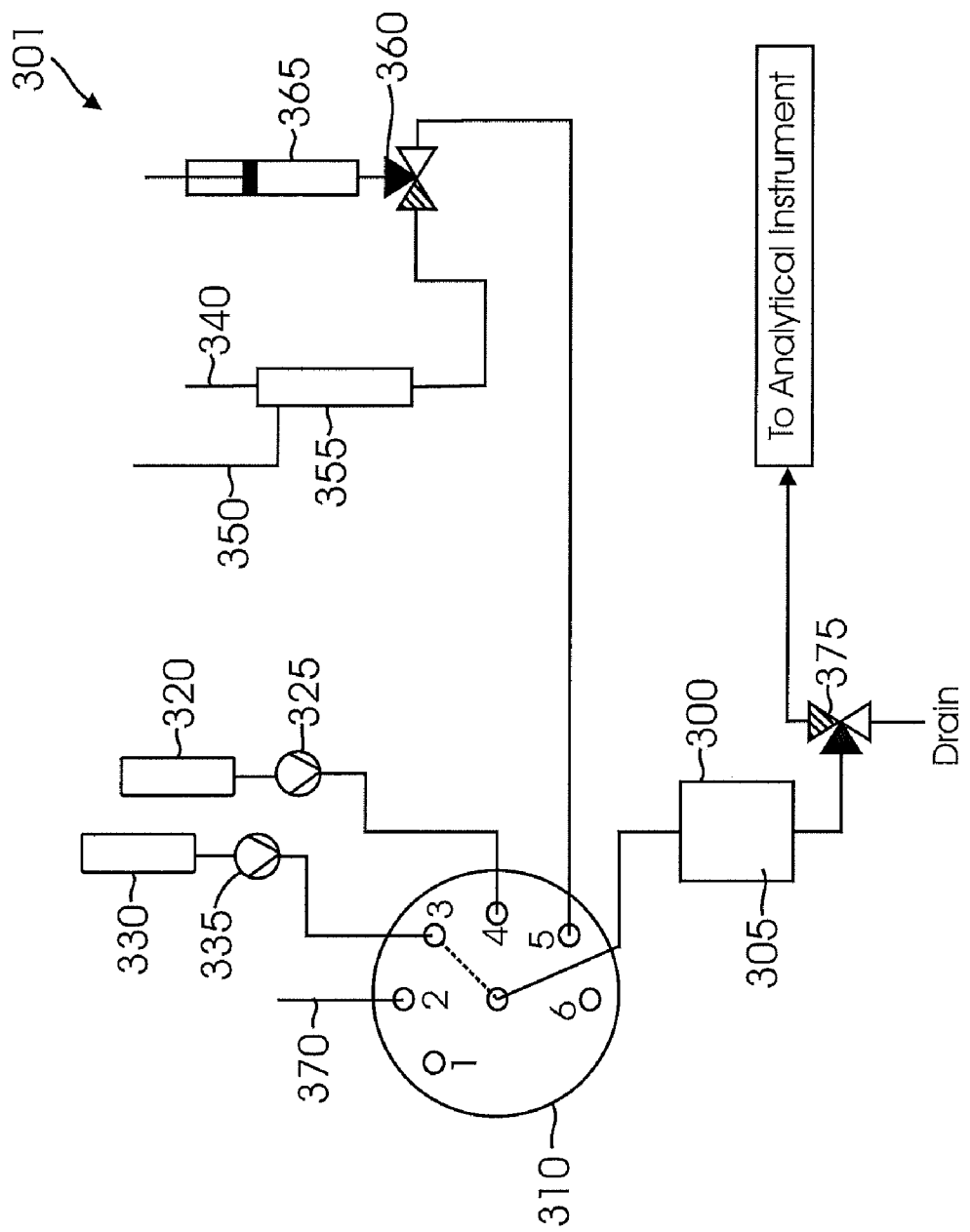
FIG. 3 shows a diagram illustrating an apparatus for neutralizing acidic matrices having in accordance with an embodiment of the invention.

Referring now to FIG. 3, an exemplary matrix elimination apparatus 301 that incorporates a column 300 packed with a weak anion exchange resin 305 is illustrated. A selection valve 310 selects for a solution to enter column 300. For example, if column 300 has finished eliminating an acidic matrix, it is regenerated through the control of selection valve 310 to select for a suitable base such as a dilute ammonium hydroxide solution 320 (such as a 2.0 M solution). A pump 325 may then pump ammonium hydroxide solution 320 into column 300. Selection valve 310 may then be controlled to select for a suitable weakly acidic metal complexing reagent such as dilute acetic acid solution 330. A pump 335 may then pump dilute acetic acid solution 330 into column 300 to activate resin 305.

A solution 340 having a harsh acid matrix such as an SC2 solution in which trace metals are desired to be characterized may be spiked using a spike 350 and allowed to equilibrate in a reservoir 355. The nature of the spike depends upon the type of analysis being performed. For example, in an IDMS technique, the spike would alter the isotopic ratio of the analyte being detected or characterized. Alternatively, in an internal standard technique, the spike would contain a homologue to the analyte being detected or characterized. In either case, the spike has a known concentration such that the analyte (the metal(s) of interest) may be characterized using a ratio measurement. A three-way valve 360 may then be switched to allow a pump such as a syringe pump 365 to withdraw a portion of the equilibrated spiked sample in reservoir 355. Three way valve 360 and selection valve 310 may then be controlled so as to allow pump 365 to pump the withdrawn portion into column 300. The treated spiked sample from column 300 will thus have its acidic matrix eliminated and trace metals stabilized. The trace metals may then be characterized in a corresponding analytical instrument such as a mass spectrometer (not illustrated). To prevent effluent from column 300 during the regeneration and activation acts from entering the analytical instrument, a valve such as a 3-way valve 375 at the outlet of column 300 may select for a drain during these acts. However, when the treated sample flows from column 300, 3-way valve 375 would select for the analytical instrument. Column 300 may be flushed with ultra pure water (UPW) 370 as necessary such as after the activation act. In this fashion, samples 340 may be analyzed continually 24 hours per day for several months without changing column 300. In one example, trace metals Na+, Ca+2, Cu+2 may be detected in the range of 10 ppb (parts per billion) in 5% H2SO4 having a pH <2. To form the column, 5.6 gram of weak anion exchange resin in free base form was packed into a 2"×0.2" PEEK tubing. The resin was then activated by flowing 10 ml of 0.5M acetic through the column. Excess acetic acid was then washed from the column with UPW. Then 2 ml of sample matrix was treated through the activated resin bed. The treated ample matrix elutes from the column at a pH of 6.7, near to neutral as can be tested by any analytical instrument.

Figure 4:
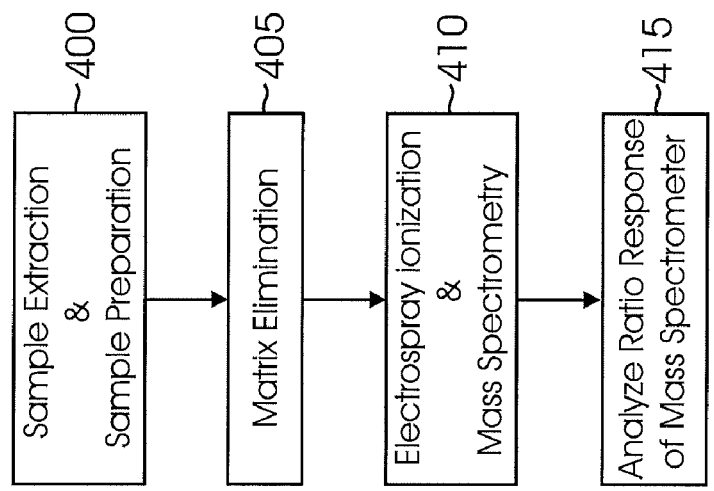
FIG. 4 is a flow chart for an IPMS process incorporating a matrix elimination apparatus in accordance with an embodiment of the invention.

As discussed above, the IPMS technique permits automated analysis of both trace contaminants and constituents in liquid and gaseous solutions. An exemplary IPMS tool for trace analysis is disclosed in U.S. application Ser. No. 10/086,025, filed Feb. 28, 2002, now U.S. Pat. No. 7,220,383, the contents of which are hereby incorporated by reference. The machine control disclosed in U.S. application Ser. No. 10/086,025 is readily modified to control a matrix elimination apparatus such as described with respect to FIG. 3. The resulting IPMS process flow is shown in FIG. 4. In step 400, the sample is extracted from, for example, a process solution. Spikes are often unstable in the ppb concentration range yet should be roughly at the same concentration as the metal ions to be characterized. Thus, step 400 also includes the dilution of the spike as discussed in U.S. application Ser. No. 10/086,025. The resulting spike and extracted sample may then have its acidic matrix eliminated in step 405 as discussed, for example, with respect to FIG. 3. The treated spiked sample may then be electrospray ionized and processed in a mass spectrometer in step 410. In step 415, a ratio response from the mass spectrometer is analyzed to determine a trace metal ion(s) concentration in the sample.

The above-described embodiments of the present invention are merely meant to be illustrative and not limiting. Various changes and modifications may be made without departing from this invention in its broader aspects. Therefore, the appended claims encompass all such changes and modifications as falling within the true spirit and scope of this invention.

I claim:

1. A method of neutralizing the matrix of an acidic solution including at least one metal using a weak anion exchange resin, comprising:
    activating the weak anion exchange resin with a weakly acidic metal complexing reagent, the weakly acidic metal complexing reagent partially disassociating into protons and metal complexing anions, whereby some functional groups in the weak anion exchange resin are protonated and bind with the metal complexing anions; and
    neutralizing a sample of the acidic solution with the activated weak anion exchange resin, wherein the bound metal complexing anions disassociate with the weak anion exchange resin and bind with the at least one metal, whereby the at least one metal is stabilized in a resulting neutralized sample.

2. The method of claim 1, further comprising:
    subsequent to the neutralizing act, regenerating the weak anion exchange resin with a strongly basic solution.

3. The method of claim 2, wherein the strongly basic solution is ammonium hydroxide.

4. The method of claim 1, wherein the weakly acidic metal complexing reagent is selected from the group consisting of formic acid, acetic acid, oxalic acid, glycolic acid, ethylenediaminetetraacetic acid (EDTA), nitrotriacetic acid (NTA), diethylenetriaminepentaacetic acid (DTPA), ethylenediamine (EDA), glycine, and iminodiacetic acid (IDA).

5. The method of claim 1, wherein the functional groups are selected from the group consisting of secondary and tertiary amines.

6. The method of claim 1, further comprising:
spiking a sample; and
sampling the spiked sample to produce the sample of the acidic solution.

7. The method of claim 6, further comprising:
ionizing the neutralized sample; and
processing the ionized neutralized sample in a mass spectrometer to characterize a concentration of the at least one metal.

8. The method of claim 7, wherein the ionizing act comprises electrospray ionizing the neutralized sample.

9. The method of claim 1, further comprising: analyzing a concentration of the at least one metal in the neutralized sample using a method selected from group consisting of ion chromatography, capillary electrophoresis, colorimetry, atomic absorption, optical fluorescence, inductively-coupled-plasma mass spectrometry, optical absorption, and inductively coupled plasma—optical emission spectrometry (ICP-QES).

10. A matrix elimination apparatus, comprising:
a column packed with a weak anion exchange resin; and
at least one selection valve, the at least one selection valve being configured to select between a source of a weakly acidic metal complexing agent and a source of a acidic solution including at least one trace metal such that the weakly acidic metal complexing agent and the acidic solution may sequentially flow through the column, the acidic solution thereby being neutralized and the at least one metal thereby being stabilized in a resulting neutralized solution, and an analytical instrument configured to characterize a concentration of the at least one metal in the neutralized solution.

11. The matrix elimination apparatus of claim 10, wherein the at least one selection valve is further configured to select for a basic solution for regenerating the weak anion exchange resin.

12. The matrix elimination apparatus, of claim 10, wherein the analytical instrument comprises an exchange chromatography column.

13. The matrix elimination apparatus, of claim 10, wherein the analytical instrument comprises a mass spectrometer.

14. The matrix elimination apparatus of claim 13, further comprising an electrospray ionizer to ionize the neutralized sample for introduction into the mass spectrometer.

15. A method of characterizing at least one metal in an acidic solution, comprising:
sampling the acidic solution;
spiking the sample;
activating a weak anion exchange resin with a weakly acidic metal complexing reagent selected from the group consisting of of formic acid, acetic acid, oxalic acid, glycolic acid, ethylenediaminetetraacetic acid (EDTA), nitrotriacetic acid (NTA), diethylenetriaminepentaacetic acid (DTPA), ethylenediamine (EDA), glycine, and iminodiacetic acid (IDA);
neutralizing the spiked sample with the activated weak anion exchange resin; and
characterizing the concentration of the at least one metal in the neutralized spiked sample using a ratio measurement.

16. The method of claim 15, wherein the characterizing act comprises:
ionizing the neutralized spiked sample into ions;
obtaining a mass spectrum from the ions using a mass spectrometer, wherein the ratio measurement is formed from the mass spectrum.

17. The method of claim 16, wherein the ionizing act comprises electrospray ionizing.

18. The method of claim 15, wherein the acidic solution comprises a semiconductor processing solution.

19. The method of claim 18, wherein the semiconductor processing solution comprises SC2.

* * * * *